United States Patent
Rowe et al.

(10) Patent No.: US 9,168,359 B2
(45) Date of Patent: Oct. 27, 2015

(54) MODULAR INTRODUCER AND EXCHANGE SHEATH

(75) Inventors: Douglas Rowe, San Jose, CA (US); Scott McIntosh, Sunnyvale, CA (US); Dawn Ma, San Jose, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 949 days.

(21) Appl. No.: 11/427,301

(22) Filed: Jun. 28, 2006

(65) Prior Publication Data

US 2007/0005001 A1    Jan. 4, 2007

Related U.S. Application Data

(60) Provisional application No. 60/695,464, filed on Jun. 30, 2005.

(51) Int. Cl.
*A61M 39/00* (2006.01)
*A61M 25/06* (2006.01)
*A61M 25/00* (2006.01)

(52) U.S. Cl.
CPC ....... *A61M 25/0662* (2013.01); *A61M 25/0014* (2013.01); *A61M 25/0075* (2013.01); *A61M 25/0097* (2013.01); *A61M 2025/0098* (2013.01)

(58) Field of Classification Search
CPC ..................... A61M 25/0014; A61M 25/0097; A61M 2025/0098
USPC ................. 600/184; 604/104, 164.01, 167.03
See application file for complete search history.

(56) References Cited

U.S. PATENT DOCUMENTS

| | | |
|---|---|---|
| 883,583 A | 3/1908 | Stallsmith |
| 1,696,018 A | 12/1928 | Schellberg |
| 2,548,602 A | 4/1951 | Greenburg |
| 4,143,853 A | 3/1979 | Abramson |
| 4,406,656 A | 9/1983 | Hattler et al. |

(Continued)

FOREIGN PATENT DOCUMENTS

| | | | |
|---|---|---|---|
| WO | 98/13083 | 4/1998 | |
| WO | WO 9813083 A1 * | 4/1998 | .......... A61M 5/0178 |

(Continued)

OTHER PUBLICATIONS

U.S. Appl. No. 11/767,947, Aug. 20, 2010, Office Action.

(Continued)

*Primary Examiner* — Diane Yabut
(74) *Attorney, Agent, or Firm* — Workman Nydegger; Randy Shen

(57) ABSTRACT

In accordance with the present invention there is provided exemplary embodiments of an introducer sheath in accordance with the present invention, wherein the introducer sheath of the present invention is formed of multiple components which are resiliently assembled to form a single introducer sheath. One embodiment of the introducer sheath includes a hub, a retaining member and an elongated tubular member. The hub has a lumen that has a groove. The elongated tubular member has a proximal end that includes a flared portion. The distal end of the retaining member is configured to be received in the groove formed in the lumen of the hub. The distal end of the retaining member contacts the flared portion of the tubular member when distal end of the retaining member is disposed in the groove such that the tubular member is retained within the lumen of the hub in a sealed engagement.

25 Claims, 11 Drawing Sheets

(56) References Cited

U.S. PATENT DOCUMENTS

| | | | |
|---|---|---|---|
| 4,411,655 A | 10/1983 | Schreck | |
| 4,451,256 A | 5/1984 | Weikl et al. | |
| 4,574,173 A | 3/1986 | Bennett | |
| 4,596,559 A | 6/1986 | Fleischhacker | |
| 4,601,713 A | 7/1986 | Fuqua | |
| 4,619,643 A | 10/1986 | Bai | |
| 4,747,833 A | 5/1988 | Kousai et al. | |
| 4,899,729 A * | 2/1990 | Gill et al. | 606/198 |
| 4,950,257 A | 8/1990 | Hibbs et al. | |
| 4,983,168 A | 1/1991 | Moorehead | |
| 5,106,054 A | 4/1992 | Mollenauer et al. | |
| 5,106,368 A | 4/1992 | Uldall et al. | |
| 5,176,652 A | 1/1993 | Littrell | |
| 5,176,659 A | 1/1993 | Mancini | |
| 5,180,372 A | 1/1993 | Vegoe et al. | |
| RE34,327 E | 7/1993 | Kreamer | |
| 5,244,619 A | 9/1993 | Burnham | |
| 5,250,033 A | 10/1993 | Evans et al. | |
| 5,320,611 A | 6/1994 | Bonutti et al. | |
| 5,354,280 A | 10/1994 | Haber et al. | |
| 5,423,774 A | 6/1995 | Fischell et al. | |
| 5,447,503 A | 9/1995 | Miller | |
| 5,464,398 A | 11/1995 | Haindl | |
| 5,466,230 A | 11/1995 | Davila | |
| 5,558,737 A | 9/1996 | Brown et al. | |
| 5,584,803 A | 12/1996 | Stevens et al. | |
| 5,647,846 A | 7/1997 | Berg et al. | |
| 5,674,240 A | 10/1997 | Bonutti et al. | |
| 5,693,025 A | 12/1997 | Stevens | |
| 5,749,889 A | 5/1998 | Bacich et al. | |
| 5,795,326 A | 8/1998 | Simán | |
| 5,823,961 A | 10/1998 | Fields et al. | |
| 5,827,227 A | 10/1998 | Delago | |
| 5,910,155 A | 6/1999 | Ratcliff et al. | |
| 5,944,691 A | 8/1999 | Querns et al. | |
| 5,957,902 A | 9/1999 | Teves | |
| 5,964,730 A | 10/1999 | Williams et al. | |
| 5,968,009 A | 10/1999 | Simán | |
| 5,993,436 A | 11/1999 | Kitou et al. | |
| 6,190,357 B1 | 2/2001 | Ferrari et al. | |
| 6,192,568 B1 | 2/2001 | Kafrawy et al. | |
| 6,224,586 B1 | 5/2001 | Stephens | |
| 6,280,433 B1 | 8/2001 | McIvor et al. | |
| 6,312,374 B1 | 11/2001 | von Hoffmann | |
| 6,358,266 B1 | 3/2002 | Bonutti | |
| 6,416,499 B2 | 7/2002 | Paul, Jr. | |
| 6,419,624 B1 | 7/2002 | Burton et al. | |
| 6,450,987 B1 | 9/2002 | Kramer | |
| 6,497,721 B2 | 12/2002 | Ginsburg et al. | |
| 6,616,678 B2 | 9/2003 | Nishtala et al. | |
| 6,630,086 B1 | 10/2003 | Goral et al. | |
| 6,712,791 B2 | 3/2004 | Lui et al. | |
| 6,749,600 B1 | 6/2004 | Levy | |
| 6,827,710 B1 | 12/2004 | Mooney et al. | |
| 6,849,062 B2 | 2/2005 | Kantor | |
| 6,887,417 B1 | 5/2005 | Gawreluk et al. | |
| 6,923,788 B2 | 8/2005 | Kantor | |
| 6,945,990 B2 | 9/2005 | Greenan | |
| 7,144,386 B2 | 12/2006 | Korkor et al. | |
| 7,637,893 B2 | 12/2009 | Christensen et al. | |
| 7,699,864 B2 | 4/2010 | Kick et al. | |
| 7,713,193 B2 | 5/2010 | Nance et al. | |
| 7,727,179 B2 | 6/2010 | Barrett | |
| 7,762,995 B2 | 7/2010 | Eversull et al. | |
| 7,896,897 B2 * | 3/2011 | Gresham et al. | 606/191 |
| 7,967,830 B2 | 6/2011 | Ayala et al. | |
| 7,974,710 B2 | 7/2011 | Seifert | |
| 8,012,127 B2 | 9/2011 | Lieberman et al. | |
| 2001/0049499 A1 | 12/2001 | Lui et al. | |
| 2002/0010425 A1 | 1/2002 | Guo et al. | |
| 2002/0032459 A1 | 3/2002 | Horzewski et al. | |
| 2002/0107482 A1 | 8/2002 | Rocamora et al. | |
| 2002/0183781 A1 | 12/2002 | Casey et al. | |
| 2003/0004537 A1 | 1/2003 | Boyle et al. | |
| 2003/0014015 A1 | 1/2003 | Tansey, Jr. et al. | |
| 2003/0032941 A1 | 2/2003 | Boyle et al. | |
| 2003/0050604 A1 | 3/2003 | Lui et al. | |
| 2004/0102738 A1 | 5/2004 | Dikeman et al. | |
| 2004/0153122 A1 * | 8/2004 | Palermo | 606/213 |
| 2005/0027257 A1 | 2/2005 | Davey | |
| 2005/0059934 A1 * | 3/2005 | Wenchell et al. | 604/167.01 |
| 2005/0059990 A1 | 3/2005 | Ayala et al. | |
| 2005/0080430 A1 | 4/2005 | Wright, Jr. et al. | |
| 2005/0085841 A1 | 4/2005 | Eversull et al. | |
| 2005/0131447 A1 | 6/2005 | Wahr et al. | |
| 2007/0224309 A1 | 9/2007 | Mejlhede et al. | |
| 2009/0054874 A1 | 2/2009 | Barron et al. | |
| 2009/0221965 A1 | 9/2009 | Osypka | |
| 2009/0264832 A1 | 10/2009 | Dikeman et al. | |
| 2009/0270989 A1 | 10/2009 | Conner et al. | |
| 2010/0094392 A1 | 4/2010 | Nguyen et al. | |
| 2010/0130936 A1 | 5/2010 | Voss | |
| 2010/0130937 A1 | 5/2010 | Voss | |
| 2010/0130939 A1 | 5/2010 | Voss | |
| 2010/0198160 A1 | 8/2010 | Voss | |
| 2010/0268163 A1 | 10/2010 | Rowe et al. | |
| 2013/0138043 A1 | 5/2013 | Voss | |
| 2013/0338595 A1 | 12/2013 | Voss | |
| 2015/0088072 A1 | 3/2015 | Voss | |

FOREIGN PATENT DOCUMENTS

| | | |
|---|---|---|
| WO | WO 98/29026 | 7/1998 |
| WO | WO 2005/018728 | 3/2005 |
| WO | WO 2009/120871 | 10/2009 |

OTHER PUBLICATIONS

U.S. Appl. No. 11/427,308, Sep. 15, 2010, Office Action.
U.S. Appl. No. 12/696,792, filed Jan. 29, 2010, Voss.
U.S. Appl. No. 12/696,837, filed Jan. 29, 2010, Voss.
U.S. Appl. No. 12/724,889, filed Mar. 16, 2010, Rowe et al.
U.S. Appl. No. 11/427,306, Aug. 21, 2009, Office Action.
U.S. Appl. No. 11/427,306, Apr. 12, 2010, Office Action.
U.S. Appl. No. 11/427,308, Sep. 29, 2009, Office Action.
U.S. Appl. No. 11/427,308, May 11, 2010, Office Action.
U.S. Appl. No. 11/767,947, Jun. 2, 2009, Office Action.
U.S. Appl. No. 11/767,947, Nov. 12, 2009, Office Action.
U.S. Appl. No. 11/767,947, Mar. 31, 2010, Office Action.
U.S. Appl. No. 11/767,947, Jul. 8, 2011, Office Action.
U.S. Appl. No. 11/427,308, Oct. 25, 2011, Office Action.
U.S. Appl. No. 12/695,969, Jan. 24, 2012, Office Action.
U.S. Appl. No. 11/767,947, Feb. 3, 2011, Office Action.
U.S. Appl. No. 12/695,961, Feb. 13, 2012, Office Action.
U.S. Appl. No. 12/695,975, Feb. 13, 2012, Office Action.
U.S. Appl. No. 12/724,889, Mar. 29, 2012, Office Action.
U.S. Appl. No. 12/696,792, Nov. 10, 2011, Office Action.
U.S. Appl. No. 11/427,306, Oct. 21, 2010, Office Action.
U.S. Appl. No. 12/696,837, Dec. 19, 2011, Office Action.
U.S. Appl. No. 11/767,947, Feb. 27, 2012, Office Action.
U.S. Appl. No. 11/427,308, Mar. 29, 2011, Office Action.
U.S. Appl. No. 12/695,961, Jan. 9, 2013, Issue Notification.
U.S. Appl. No. 12/695,969, Dec. 24, 2012, Notice of Allowance.
U.S. Appl. No. 60/695,464, filed Jun. 30, 2005, Rowe.
U.S. Appl. No. 60/695,602, filed Jun. 30, 2005, Voss.
U.S. Appl. No. 11/427,308, Jul. 19, 2012, Office Action.
U.S. Appl. No. 12/695,961, May 11, 2012, Office Action.
U.S. Appl. No. 12/695,961, Sep. 21, 2012, Notice of Allowance.
U.S. Appl. No. 12/695,969, Jul. 20, 2012, Office Action.
U.S. Appl. No. 12/695,975, May 11, 2012, Office Action.
U.S. Appl. No. 12/695,975, Oct. 5, 2012, Office Action.
U.S. Appl. No. 12/696,837, Jul. 19, 2012, Office Action.
U.S. Appl. No. 12/724,889, Oct. 26, 2012, Office Action.
U.S. Appl. No. 13/835,570, filed Mar. 15, 2013, Voss et al.
Richard Vennix, Material properties of PTFE, Engineering Polymers/Polymers Data Sheets, Matbase,<<http://www.matbase.com/material/polymers/engineering/ptfe/properties>>Jan. 25, 2010.
Richard Vennix, Material Properties of PMMA, Commodity Polymers/Polymer Data Sheets, Matbase, <<http://www.matbase.com/materials/polymers/commodity/pmma/properties>>Jan. 25, 2010.

(56) References Cited

OTHER PUBLICATIONS

U.S. Appl. No. 11/427,306, Feb. 26, 2008, Office Action.
U.S. Appl. No. 11/427,306, Mar. 5, 2009, Office Action.
U.S. Appl. No. 11/427,308, Apr. 23, 2014, Office Action.
U.S. Appl. No. 11/767,947, Nov. 27, 2013, Notice of Allowance.
U.S. Appl. No. 12/695,975, Feb. 25, 2014, Office Action.
U.S. Appl. No. 12/695,975, Jul. 14, 2014, Office Action.
U.S. Appl. No. 12/695,975, Dec. 16, 2014, Office Action.
U.S. Appl. No. 12/696,792, Dec. 27, 2013, Office Action.
U.S. Appl. No. 12/696,792, Jan. 29, 2015, Office Action.
U.S. Appl. No. 12/696,837, Apr. 25, 2014, Office Action.
U.S. Appl. No. 12/696,837, Jan. 13, 2015, Office Action.
U.S. Appl. No. 12/724,889, Mar. 21, 2014, Office Action.
U.S. Appl. No. 12/724,889, Oct. 10, 2014, Office Action.
U.S. Appl. No. 13/752,137, Mar. 10, 2014, Office Action.
U.S. Appl. No. 13/752,137, Jun. 23, 2014, Notice of Allowance.
U.S. Appl. No. 13/835,570, Jul. 28, 2014, Office Action.
U.S. Appl. No. 13/835,570, Mar. 19, 2015, Office Action.
U.S. Appl. No. 13/892,106, Mar. 26, 2014, Office Action.
U.S. Appl. No. 13/892,106, Aug. 12, 2014, Office Action.
U.S. Appl. No. 13/892,106, Nov. 28, 2014, Office Action.
U.S. Appl. No. 13/892,106, Apr. 30, 2015, Office Action.

* cited by examiner

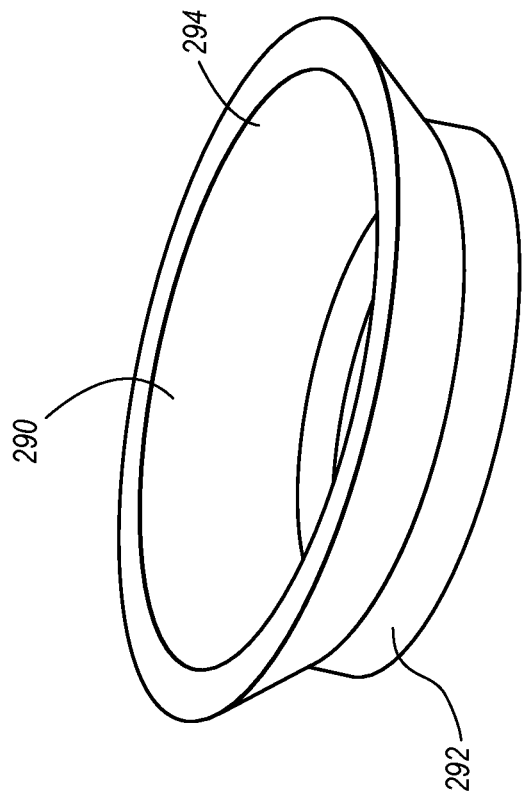
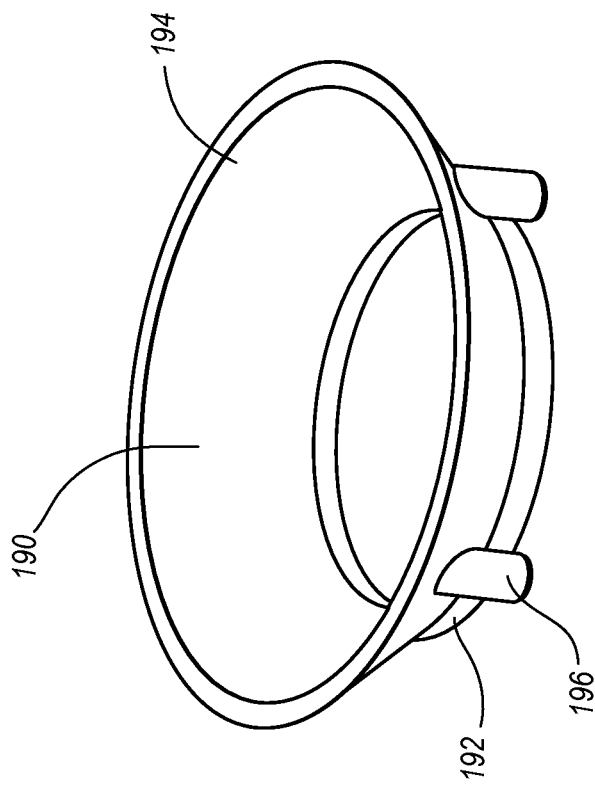
FIG. 11B
FIG. 11A

MODULAR INTRODUCER AND EXCHANGE SHEATH

CROSS-REFERENCE TO RELATED APPLICATIONS

This application claims the benefit of U.S. Provisional Application Ser. No. 60/695,464, filed Jun. 30, 2005, and entitled MODULAR INTRODUCER SHEATH, which application is hereby incorporated by reference in its entirety. This application also relates to U.S. patent application Ser. No. 11/427,306, filed Jun. 28, 2006, and entitled "Introducer Sheath" and U.S. patent application Ser. No. 11/427,308, now abandoned, filed Jun. 28, 2006, and entitled "Expandable Introducer Sheath", the disclosures of which are incorporated herein by this reference.

BACKGROUND OF THE INVENTION

1. The Field of the Invention

The present invention relates generally to medical devices and methods. More specifically, the present invention relates generally to introducer sheaths and, in particular, to an introducer sheath that is assembled from individual components such that the individual components are resiliently locked together when assembled. The introducer sheath in accordance with the present invention is generally for use during minimally invasive medical procedures.

2. The Relevant Technology

A wide variety of introducer sheaths have been developed for medical use. Introducer sheaths are often used to access a vessel or artery to allow a surgical procedure to be performed. For example, introducer sheaths are often used for medical procedures that utilize catheters, such as angioplasty or stenting procedures. In practice, the introducer sheath is typically inserted into the patient's vasculature using the modified Seldinger technique. Under the Seldinger technique, a needle is first inserted into the vessel. A guidewire is then inserted through the needle and into the vessel. Next, the needle is removed and a sheath/dilator combination is advanced over the guidewire. The dilator is used to expand the puncture in the vessel to a size suitable to receive an introducer sheath. After the distal end of the sheath is disposed within the vessel, the dilator and guidewire are removed, thereby allowing access to the vessel.

Conventionally, introducer sheaths are formed of three or more components that require assembly: an elongated tubular member, a hub portion, and a hemostasis valve disposed within the hub portion. In some designs an introducer sheath may also include a strain relief member which is disposed adjacent the distal end of the hub and about the proximal end of the elongated tubular portion. A suitable example of such an assembly is shown in U.S. Pat. No. 5,807,350, which discloses an introducer sheath having a construction similar to that described above, the entirety of which is hereby incorporated herein by reference.

Introducer sheaths, such as that described above, are generally constructed of multiple pieces which must be assembled to form the sheath. In most cases, the distal end of the hub portion is molded over the elongated tubular member. While molding may produce a stronger part, there is the possibility of damaging a portion of the other components of the device during the process. Any such damage results in the entire device having to be thrown away. As a result, there is a need for a way to attach the proximal end of the tubular member to the distal end of the hub portion which still meets all of the requirements of the introducer sheath, including but not limited to forming a fluid seal and having sufficient strength between the attachment of the hub portion and the tubular member to remain attached, but does not require throwing the entire device away if a portion of the sheath is damaged during manufacturing or assembly.

Prior introducer sheaths with such a substantially unitary design had difficulty accounting for or accommodating the variations that occur in the manufacturing process. When a defect occurred, even if it is only in a portion of the sheath, the unit must be discarded resulting in higher manufacturing costs and lower yields.

Similarly, the unitary design of introducer sheaths made it difficult to change materials during the manufacturing process or even changing the design of the sheath itself. Where an overmolded process is used to create the unitary introducer sheath, all the portions of the sheath are subjected to the heat from the molding process. As a result, the manufacturing processing itself may result in an uncontrolled change in geometry or a general decrease in quality control. Thus, there is a need for a new introducer sheath having lower manufacturing costs and higher quality control while still retaining the important requirements for an introducer sheath.

In another embodiment, the introducer sheath may be manufactured to be splitable during use. That is, the elongated tubular member may have a pre-scored line or another feature that allows it to split along a pre-determined path. In these instances, the choice of the material for the tubular shaft must be balanced between being splitable and being kink resistant and providing good performance. Therefore, there is a need for an improved introducer sheath having good kink resistance and good splitting properties.

BRIEF SUMMARY OF THE INVENTION

These and other limitations are overcome by embodiments of the invention, which relates to medical devices and methods of use of, in particular, introducer sheaths. Embodiments of the invention provide several designs and methods of manufacture of the improved introducer sheath. One embodiment of the invention includes an introducer sheath formed as multiple components which can then be separately assembled to form an introducer sheath. In this embodiment, the components are assembled using resilient connections.

One embodiment of the introducer sheath includes a hub, a retaining member, and an elongated tubular member. The hub has a proximal end and a distal end with a lumen extending therebetween. In one embodiment, a portion of the lumen of the hub has a groove formed therein. The elongated tubular member has a distal end and a proximal end of which a portion is flared. The retaining member of the introducer sheath has a proximal end and a distal end configured to be received in the groove formed in the lumen of the hub. The distal end of the retaining member contacts the flared portion of the tubular member when the distal end of the retaining member is disposed in the groove such that the tubular member is retained within the lumen of the hub.

In one embodiment described above, a geometric pattern may be formed on the inner surface of the elongated tubular portion of the sheath, wherein the geometric pattern aids in splitting of the introducer sheath if desired.

The introducer sheaths disclosed herein are intended to be utilized in combination with a vessel closure device such as those shown in U.S. Pat. No. 6,197,042 and pending U.S. patent application Ser. No. 10/356,214, filed Aug. 8, 2004 entitled "Clip Applier and Methods of Use", which are both assigned to a common owner and are hereby incorporated by reference herein in their entireties.

Additional features and advantages of the present invention will be set forth in the description which follows, and in part will be obvious from the description, or may be learned by the practice of the invention as set forth hereinafter. The features and advantages of the invention may be realized and obtained by means of the instruments and combinations particularly pointed out in the appended claims.

BRIEF DESCRIPTION OF THE DRAWINGS

To further clarify the above-recited and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 11a is a perspective view of one embodiment of a locking ring used in the introducer sheath of FIG. 10.

FIG. 11b is a perspective view of an alternate embodiment of a locking ring used in the introducer sheath of FIG. 10.

DETAILED DESCRIPTION OF THE PREFERRED EMBODIMENTS

The following detailed description should be read with reference to the drawings in which similar elements in different drawings are numbered the same. The drawings, which are not necessarily to scale, depict illustrative embodiments and are not intended to limit the scope of the invention.

In accordance with the present invention, an introducer sheath formed as multiple components which can then be separately assembled to form an introducer sheath. In one embodiment, the components are assembled using a resilient engagement. In one embodiment, the introducer sheath comprises a hub having a proximal end and a distal end. The proximal end of the hub is configured to receive a flexible membrane or valve therein. The introducer sheath further includes an elongated tubular member generally extending from the distal portion of the hub. The elongated tubular member is generally centered with an axis of the hub.

Figure 1:
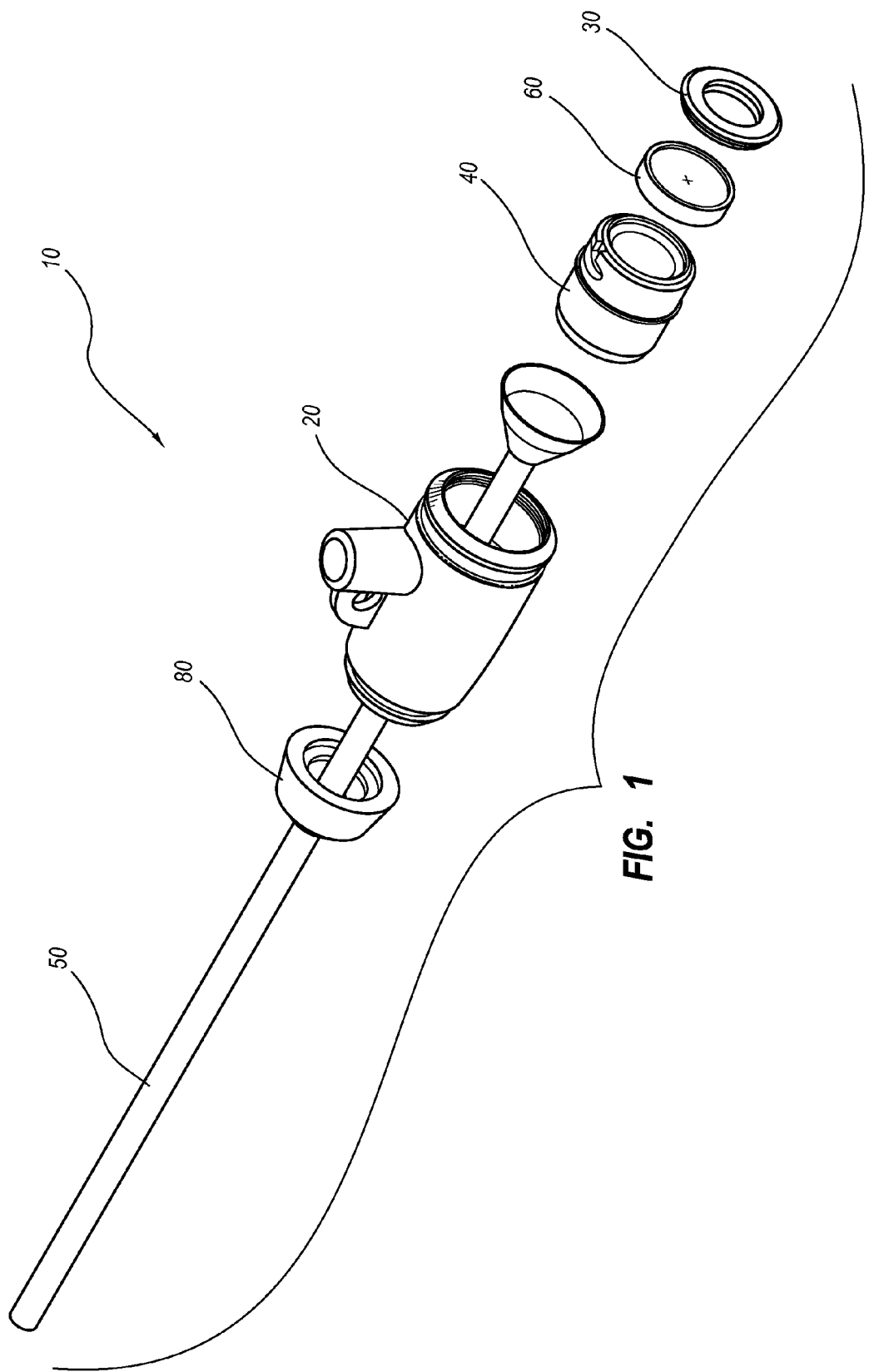
FIG. 1 is an exploded perspective view of an exemplary embodiment of an introducer sheath.
Figure 2:
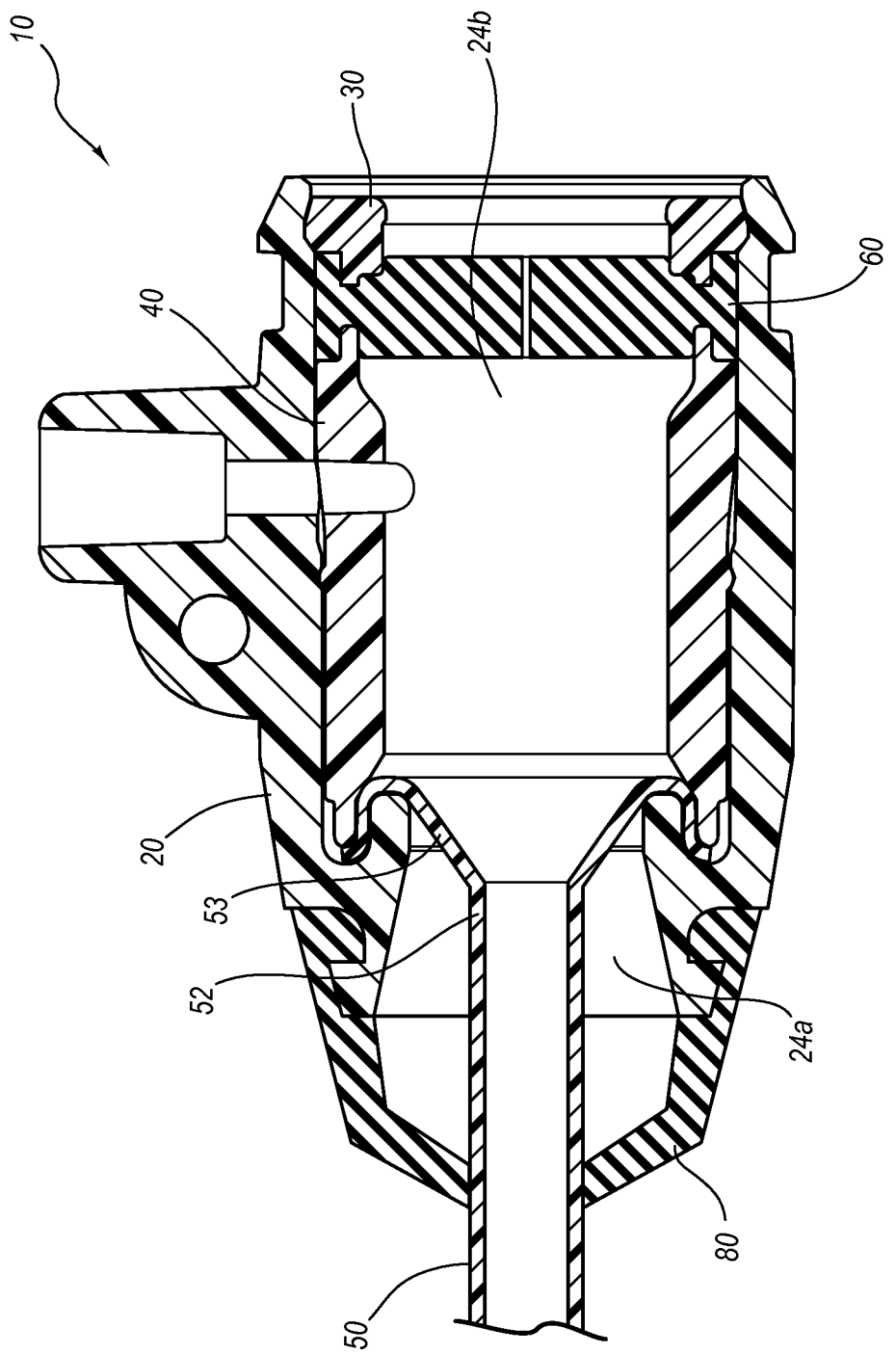
FIG. 2 is a partial cross-sectional view of one embodiment of an assembled introducer sheath in accordance with the present invention.

FIG. 1 depicts an exploded view of the individual components of one embodiment of an introducer sheath 10. FIG. 2 illustrates a cross-sectional view of an exemplary embodiment of an assembled introducer sheath 10 in accordance with the present invention. As shown in FIGS. 1 and 2, the introducer sheath 10 includes a hub 20, a cap 30, a retainer 40, and a generally elongate tubular member 50 extending outwardly from one end of the hub 20. The introducer sheath 10 also includes a flexible membrane or hemostasis valve 60. As illustrated in FIGS. 1 and 2, introducer sheath 10 includes an optional strain relief member 80.

Figure 3:
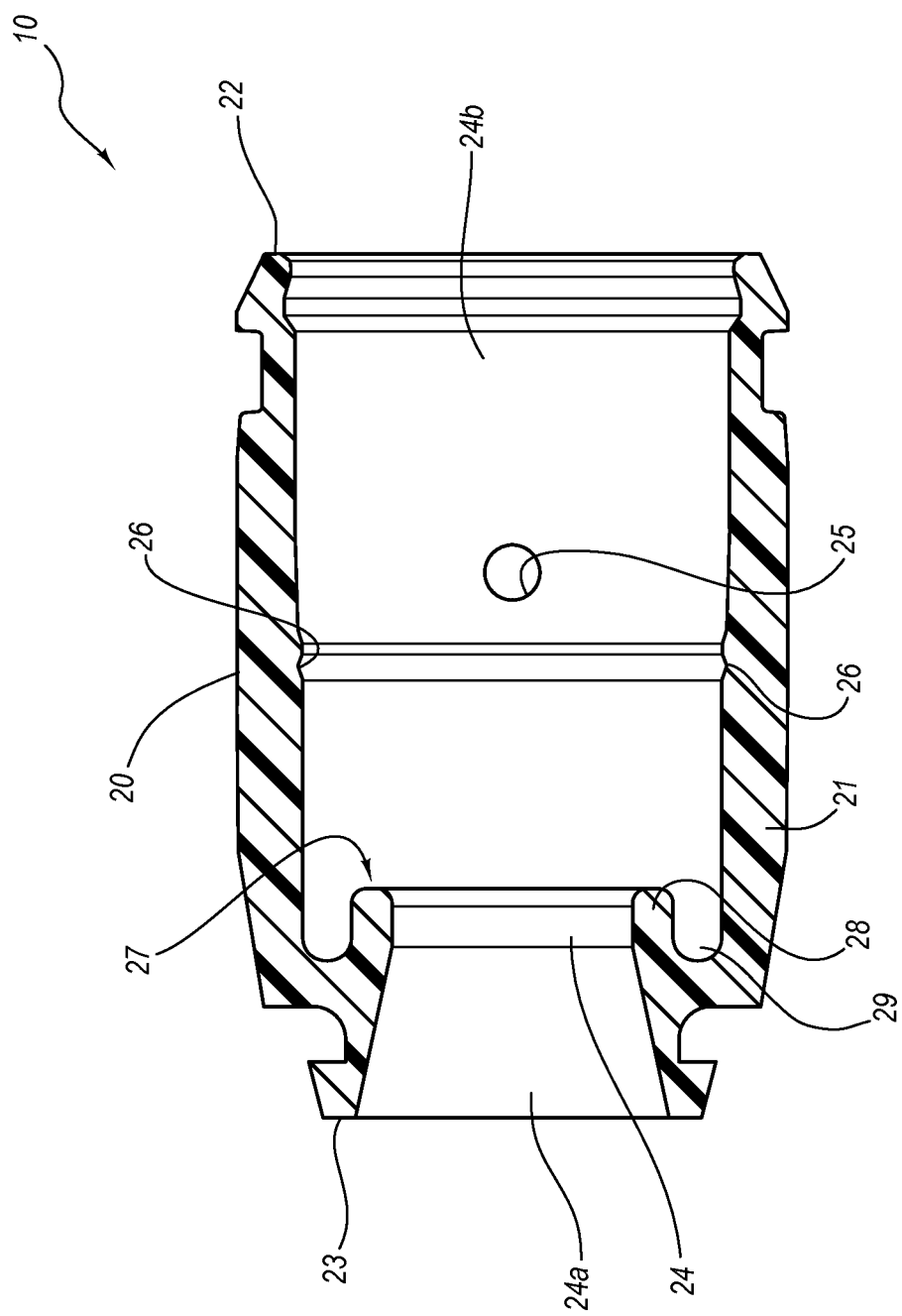
FIG. 3 is a cross-sectional view of one embodiment of a hub of the introducer sheath of FIG. 2 in accordance with the present invention.

As shown in further detail in FIG. 3, the hub 20 includes a main body 21 having a proximal end 22 and a distal end 23 and a central lumen 24 extending therebetween. In one possible embodiment, a port 25 may be provided in the side of the main body 21 of hub 20. The port 25 formed in the main body 21 of the hub 20 is in fluid communication with the central lumen 24 extending between the proximal end 22 and the distal end 23 of the main body 21 of hub 20.

In an exemplary embodiment depicted in FIG. 3, the central lumen 24 comprises a first lumen portion 24a and a second lumen portion 24b. The first lumen portion 24a and the second lumen portion 24b can have a common central axis. It will be appreciated by one skilled in the art that first lumen portion 24a and second lumen portion 24b are not required to have a common central axis. The first lumen portion 24a is proximate to the distal end 23 of the hub 20 while the second lumen portion 24b is proximate to the proximal end 22 of the hub 20. As illustrated in FIG. 2, the first lumen portion 24a is sized and configured so as to receive the proximal end 52 of the tubular member 50 therein. Similarly, the second lumen portion 24b is sized and configured to receive the retainer 40, the flexible member 60, and the cap 30 therein.

Returning to FIG. 3, in one embodiment the first lumen portion 24a and the second lumen portion 24a are of differing size. In this embodiment, the first lumen portion 24a is smaller than the second lumen portion 24b. As a result, the interior surface of the hub 20, which is defined by the diameters of the first lumen portion 24a and second lumen portion 24b has a shoulder area 27 in which the first lumen portion 24a transitions to the second lumen portion 24b. The shoulder area 27 may have various configurations as long as it is configured to cooperate with the proximal end 52 of the tubular member 50 and the distal end of the retainer 40 (see FIG. 2), as will be discussed in more detail below.

In an exemplary embodiment illustrated in FIG. 3, the shoulder area 27 includes a ridge 28 and a groove 29. The ridge 28 and the interior surface of the main body 21 of the hub 20 define the groove 29. The groove 29 may have various shapes and configurations as long as it is configured to receive the distal end of retainer 40 and cooperate with the proximal end 52 of the tubular member 50 as depicted in FIG. 2 and will be discussed in more detail below. In one embodiment depicted in FIG. 3, the groove 29 is a generally U-shaped channel. Alternatively, by way of example and not limitation, the groove 29 could be V-shaped, rounded, squared, tapered, or any combination thereof as long as it is configured to cooperate with retainer 40.

As illustrated most clearly in FIG. 3, in one exemplary embodiment ridge 28 is generally rectangular in shape. It will be appreciated that ridge 28 could have various shapes and configurations and perform the function thereof. By way of example and not limitation, ridge 28 could be square, round, or oval shaped or have an angular surface, or any combination thereof, as long as it is configured to cooperate with the proximal end of tubular member 50. In another embodiment, a portion of ridge 28 closest to the central axis of the hub 20 has been removed thereby forming an angled surface. In this embodiment, the angled surface of the ridge cooperates with the proximal end 52 of elongated tubular member 50.

As illustrated in FIG. 3, the second lumen portion 24b of the central lumen 24 formed in the hub 20 includes features formed therein. As will be described in detail below the features formed in the second lumen portion 24b are configured to receive various corresponding components of the introducer sheath 10.

Returning now to FIG. 2, as previously mentioned, the second lumen portion 24b of the central lumen 24 of the hub 20 is configured to receive the retainer 40 therein. The retainer 40 is configured to be detachably received within the central lumen 24 of the hub 20. More specifically, as illustrated in FIG. 2, the retainer 40 resiliently cooperates with the interior surface of the main body 21 of the hub 20. It will be appreciated that the outer surface of the retainer 40 could have various configurations as long as the retainer 40 is sized and configured to be received with second lumen portion 24b of central lumen 24. In one possible embodiment, the retainer 40 is also sized and configured so as to be resiliently retained within the second lumen portion 24b of the central lumen 24 of the hub 20.

Figure 4:
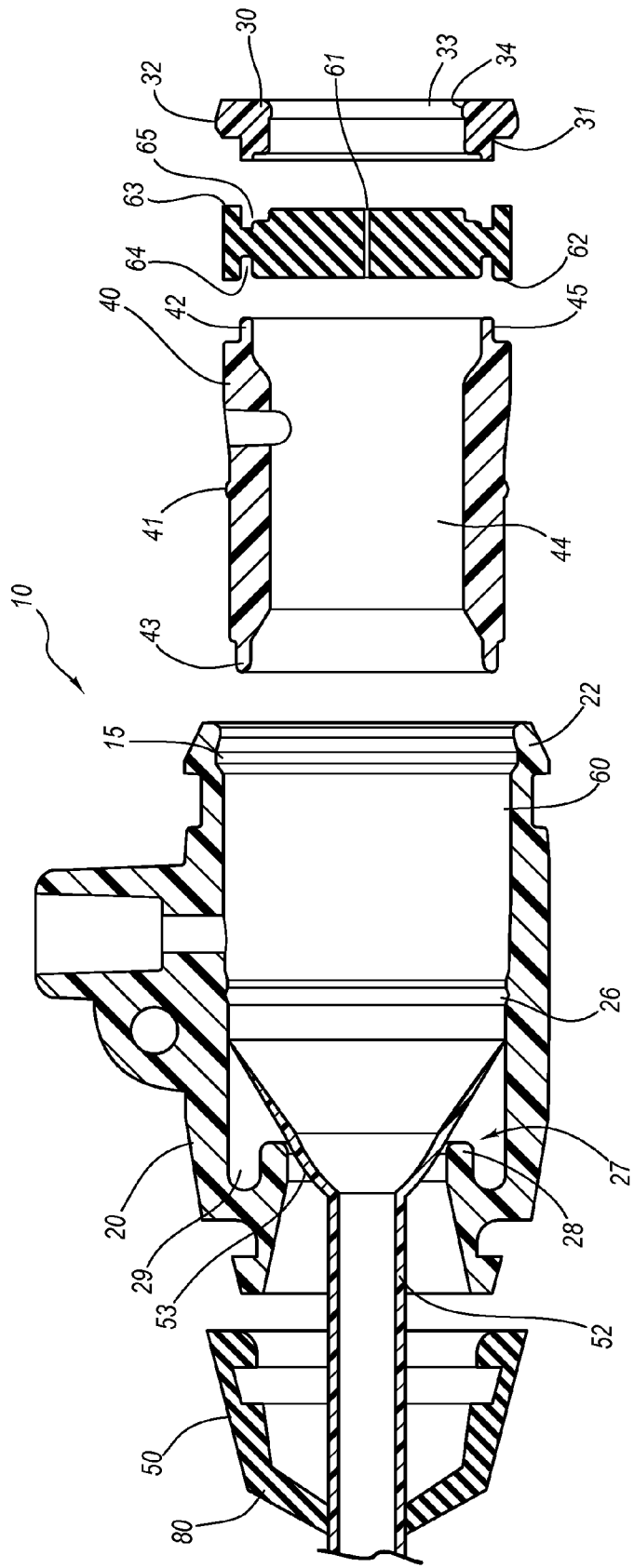
FIG. 4 is a partially exploded, cross-sectional view of the introducer sheath of FIG. 2 illustrating the individual components partially assembled to form the introducer sheath in accordance with the present invention.

FIG. 4 illustrates a cross-sectional view of one embodiment of the retainer 40 in accordance with the present invention. In one embodiment depicted in FIG. 4, the proximal end 42 of the retainer 40 is tapered outwardly so as to resiliently or frictionally engage the interior surfaces of the hub 20. In an exemplary embodiment, the retainer 40 includes locking features 41 formed in the outside surface of the retainer 40. The locking features 41 are configured to be received in corresponding locking features 26 formed in the interior surface of the main body 21 of the hub 20 as depicted in FIGS. 2 and 4.

In one embodiment illustrated, the locking features 41 and 26 are depicted as being generally rounded in shape. It will be appreciated that the locking features 41 and 26 could have various other configurations so long as they cooperate together in a resilient or frictional engagement and the locking features 41 are received into the corresponding locking features 26. By way of example and not limitation, the locking features 41 and 26 could be ovular, square, rectangular, angular, or various other shapes or combinations thereof. Further, the locking features 41 and 26 could be resilient members that slightly deflect until they snap into place. It will be appreciated by one skilled in the art that while in one embodiment retainer 40 is resiliently engaged in lumen 24 of the hub 20 by a snap-fit or frictional engagement, various other methods of attachment could be utilized, such as welding, adhesives, mechanical fasteners and the like.

One skilled in the art will also appreciate that while in the embodiment illustrated the locking features 41 of the retainer 40 protrude and are received in corresponding locking features 26 in the hub 20, they could be reversed such that the locking features 26 of the hub 20 are received into the locking feature 41 of the retainer. The importance is that the locking features 41 and 26 cooperate so as to resiliently engage and hold the retainer 40 in place in the hub 20.

Figure 6:
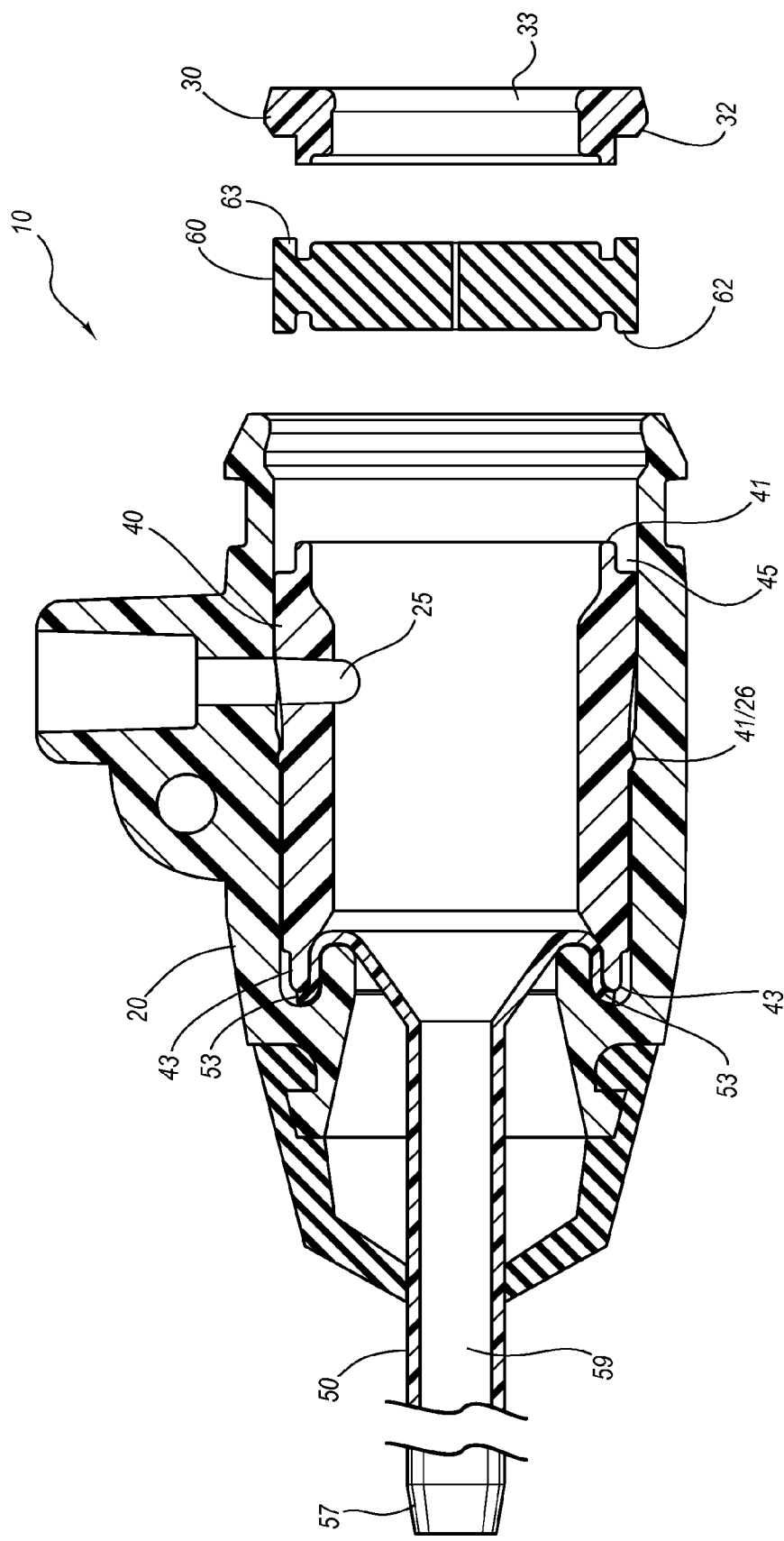
FIG. 6 is a partially exploded, cross-sectional view of the introducer sheath of FIG. 2 illustrating the components further partially assembled to form a sheath in accordance with the present invention.

As shown in FIG. 4, the retainer 40 includes a proximal end 42 and a distal end 43 with a lumen 44 extending therebetween. The proximal end 42 of the retainer 40 is configured to receive the flexible membrane or hemostasis valve 60 therein as shown in FIG. 2. As illustrated in FIGS. 2, 4, and 6, the distal end 43 of the retainer 40 is configured to be received within the shoulder area 27 of the hub 20. In particular, the distal end 43 of the retainer 40 is configured to be disposed in the groove 29 of the shoulder area 27. As illustrated in FIGS. 2 and 4, the distal end 43 of the retainer 40 is configured to cooperate with the proximal end 52 of the tubular member 50 and the groove 29 in the shoulder area 27 of the hub 20 so as to retain the proximal end 52 of the elongated tubular member 50, as will be described in greater detail below. In one embodiment, the interior surface of the distal end 43 of the retainer 40 has optional angular ridges or teeth-like features (not shown) formed therein that are configured to contact and engage proximal end of the tubular member 50.

Turning back to FIG. 4, the flexible membrane 60 includes an opening or a plurality of slits formed therein to form an opening 61. The opening 61 allows a medical device to pass through the flexible membrane 60. It will be appreciated by one skilled in the art that the opening 61 of the flexible membrane 60 may have various other configurations and perform the functions thereof. The flexible membrane 60 and the opening 61 are sized and configured to form a fluid tight seal about the medical device. Flexible membranes of this type are commonly referred to as hemostasis valves.

The flexible membrane 60 is configured to cooperate with the proximal end 42 of the retainer 40. More specifically, in one exemplary embodiment, the proximal end 42 of the retainer 40 has a recess 45 formed therein configured to receive the distal end 62 of the flexible membrane 60. It will be appreciated that the recess 45 could have various other configurations as long as it is configured to cooperate with the distal end 62 of the flexible membrane 60. In one embodiment depicted in FIG. 4, the recess 45 is a generally square shaped. Alternatively, by way of example and not limitation, the recess 45 could be rounded, oval, rectangular tapered, or any combination thereof as long as it is configured to cooperate with the distal end 62 of the flexible membrane 60.

As illustrated in FIG. 4, in one embodiment, correspondingly distal end 62 of the flexible membrane 60 has an opening 64 formed therein configured to cooperate with the proximal end 42 of the retainer 40. It will be appreciated by one skilled in the art that the distal end 62 of the flexible membrane 60, including opening 64, and the proximal end 42 of the retainer 40, including recess 45, could have various other configurations and shapes as long as they are configured to cooperate and have a sealing engagement. Alternatively, by way of example and not limitation, the opening 64 of the flexible membrane 60 and proximal end 42 of the retainer 40 could be U-shaped, round, square, oval, elliptical, tapered, or any combination thereof as long as they are configured to cooperate.

As shown in FIG. 2, the flexible membrane 60 is retained between the retainer 40 and the cap 30. An exemplary embodiment of the cap 30 of the present invention is illustrated in FIG. 4. In one embodiment, the cap 30 is configured to cooperate with the proximal end 63 of the flexible membrane 60. In particular, in this embodiment the exterior surface of the cap 30 has the recess 31 formed therein which is configured to receive the proximal end 63 of the flexible membrane 60. Similarly, the proximal end 63 of the flexible member 60 has an opening 65 formed therein configured to receive portion 36 of the cap 30. It will be appreciated by one skilled in the art that the distal portion 36 of the cap 30 and the opening 65 in the proximal end 63 of the flexible membrane 60 can have various other configurations and shapes as long as they are configured to cooperate and have a sealing engagement. Alternatively, by way of example and not limitation, that the distal portion 36 of the cap 30 and the opening 65 in the proximal end 63 of the flexible membrane 60 could be U-shaped, round, rectangular square, oval, elliptical, tapered, or any combination thereof as long as they are configured to cooperate.

It will be appreciated that the recess 31 could have various other configurations as long as the proximal end 63 of the flexible membrane 60 and the recess 31 are correspondingly shaped to cooperate. In one embodiment depicted in FIG. 4, the recess 31 is a generally square shaped. Alternatively, by way of example and not limitation, the recess 31 could be rounded, oval, rectangular tapered, or any combination thereof as long as it is configured to cooperate with the distal end 62 of the flexible membrane 60.

In one exemplary embodiment, the cap 30 when disposed over the flexible membrane 60 provides a compressive force to the flexible membrane 60, wherein the compressive force exerted on the flexible membrane 60 causes the opening 61 to be squeezed and thereby forming a more fluid tight seal therein. This compressive force however does not reduce access to or increase forces to pass a medical device through the opening 61 of the flexible membrane 60. Additionally, as described above, the compressive force exerted on the flexible membrane 60 increases the sealing of the opening 61 in a static state, the compressive force also increases the seal between the flexible membrane 61 and a medical device disposed through the opening 61 for the same reasons.

As shown in FIGS. 2 and 4, the exterior surface 32 of the cap 30 is sized and configured to be received within the proximal end 22 of the hub 20. In one embodiment illustrated in FIG. 4, the exterior surface 32 of the cap 30 is slightly angled to form a protrusion so as to be received within a corresponding cutout 15 formed on the interior surface of the proximal end 22 of the main body 21 of the hub 20. As shown in FIG. 4 the proximal end 22 of the main body 21 of the hub 20 is configured so as to resiliently move to allow the exterior surface 32 of the cap 30 to be received within the cutout 15 formed therein. In another embodiment, the exterior surface 32 of the cap 30 includes a resilient protrusion which upon the cap 30 being inserted into proximal end of the retainer 40 locks the cap 30 in place. The proximal end 22 of the main body 21 of the hub 20 includes a corresponding cutout 15 configured to receive the resilient protrusion. In either embodiment, the exterior surface 32 of the cap 30 and the interior surface of proximal end of the hub 20 are configured to cooperate such that the cap resiliently snaps into place. It will be appreciated that the exterior surface 32 of the cap 30 can have various other configurations and shapes as long as it is configured to cooperate with the proximal end 22 of the hub 20. In one exemplary embodiment, proximal end 22 of the hub 20 and the exterior surface 32 cooperate form a seal.

It will be appreciated by one skilled in the art that while in one embodiment, retainer 40 is resiliently engaged in lumen 24 of the hub 20 by a snap-fit or frictional engagement, various other methods of attachment could be utilized, such as welding, adhesives, mechanical fasteners and the like.

Figure 5:
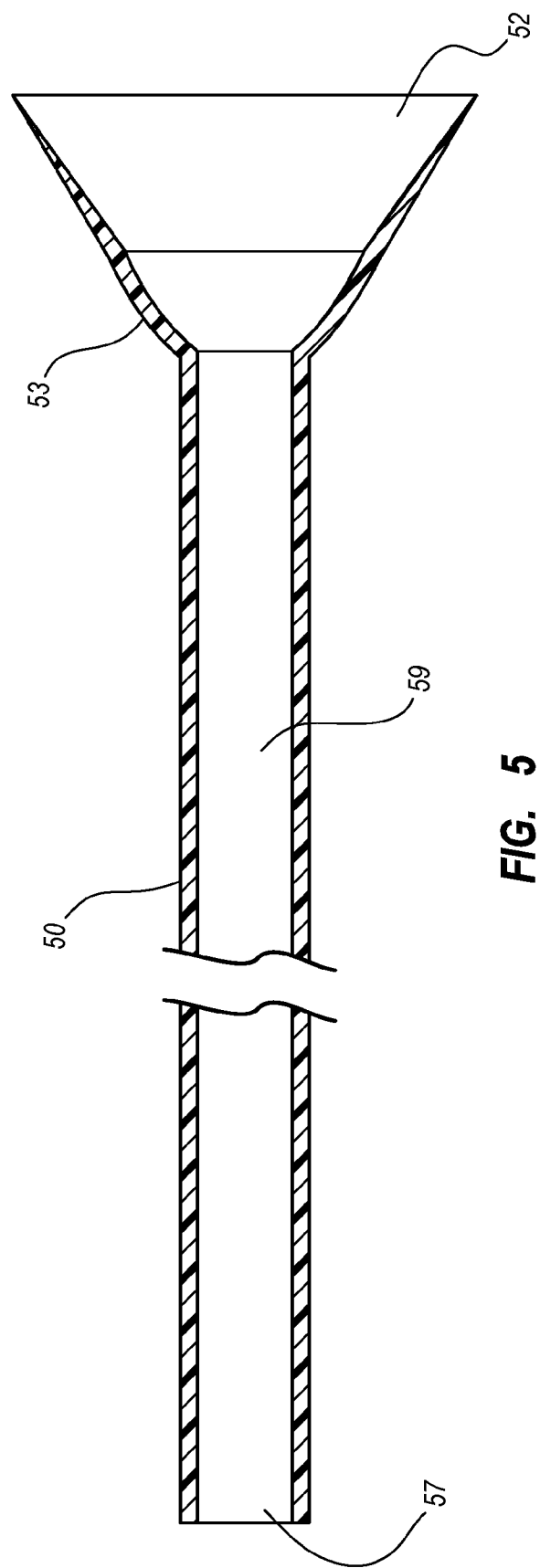
FIG. 5 a partial cross-sectional view of one embodiment of the elongated tubular member of the introducer sheath of FIG. 2 in accordance with the present invention.

FIG. 5 depicts an exemplary embodiment of the tubular member 50 in accordance with the present invention. The tubular member 50 includes a proximal end 52 and a distal end 57 with a lumen 59 extending between the two ends. In one embodiment illustrated in FIG. 5, the proximal end 52 of the tubular member 50 includes a flared portion 53 that has generally conical or flared configuration. The tubular member 50, including the flared portion 53, is comprised of a resilient flexible material. As previously mentioned the proximal end 52 of the tubular member 50 is configured to be received proximate to the distal end 23 of the hub 20 as illustrated in FIG. 4.

In particular, referring now to FIGS. 4 and 6, the flared portion 53 of the proximal end 52 of the tubular member 50 is configured to cooperate with the shoulder area 27 formed in the main body 21 of the hub 20 and the distal end 43 of the retainer 40. When the tubular member 50 is disposed in the central lumen 24 of the hub 20 and the retainer 40 is then inserted into the central lumen 24 of the hub 20, as illustrated in FIG. 6, the distal end 43 of the retainer 40 together with the ridge 28 and the groove 29 of the shoulder area 27 cooperate to retain the flared portion 53 of the distal end 52 of the tubular member 50.

It will be appreciated that the ridge 28 and the groove 29 of the shoulder area 27 of the hub 20, the distal end 43 of the retainer 40, and the flared portion 53 of the proximal end 52 of the tubular member 50 are one possible embodiment of a means for retaining tubular member 50 in the hub 20 in sealing engagement. The retaining means may also consist of the optional angular ridges or teeth-like features formed in the distal end 43 of the retainer configured to contact and engage the proximal end 52 of the tubular member 50. It will be appreciated by one skilled in the art that the retaining means may have various other configurations and perform the function thereof.

Specifically, as the retainer 40 is inserted into the hub 20, the distal end 43 of the retainer 40 contacts the flexible flared portion 53 of the proximal end 52 of the tubular member 50. In one embodiment in which the distal end 43 of the retainer 40, the teeth-like features resiliently contact the flared portion 53 of the proximal end 52 of the tubular member 50. As shown in FIG. 6, as the distal end 43 of the retainer 40 moves toward the distal end 23 of the hub 20, the flared portion 53 flexibly moves around the ridge 28 of the shoulder area 27 and the distal end 43 of the retainer 40 until both the distal end 43 of the retainer 40 and the proximal end 52 of the tubular member 50 are disposed in the groove 29. The cooperation between the distal end 43 of the retainer 40, the shoulder area 27 of the hub 20 and the proximal end 52 of the tubular member 50 forms a fluid tight seal. It will be appreciated by one skilled in the art that while in one embodiment, retainer 40 is resiliently engaged in lumen 24 of the hub 20 by a snap-fit or frictional engagement, various other methods of attachment could be utilized, such as welding, adhesives, mechanical fasteners and the like.

It will be appreciated that the proximal end 52 of the tubular member 50 may have various other configurations. The flared portion 53 may be generally conically shaped as depicted in FIG. 5. For example, the flared portion 53 at the proximal end 52 of the tubular member 50 may have various other shapes and configurations. In another embodiment, the flared portion 53 may be more cup-shaped. In addition in other alternative embodiments, flared portion 53, by way of example and not limitation, could be rounded or oval shaped, tapered, or any combination of the above-identified shapes. It will be appreciate that various other angles of the flare for flared portion 53 can be used as long as flared portion 53 is configured to cooperate with ridge 28 of shoulder area 27 and distal end 43 of retainer 40.

Figure 9:
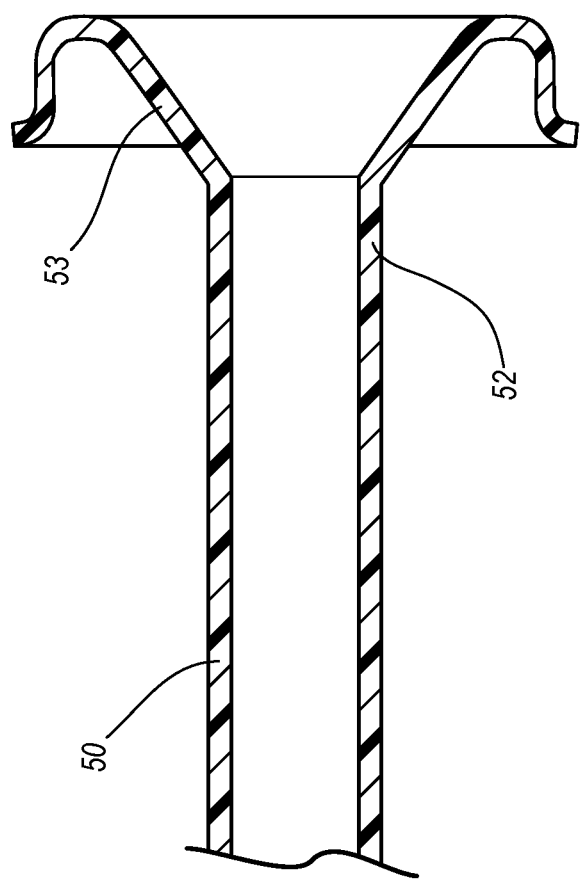
FIG. 9 is a partial cross-sectional view of an alternate embodiment of the flared portion of proximal end of an elongated tubular member of an introducer sheath in accordance with the present invention.

An alternate embodiment of the proximal end 52 of the tubular member 50 is illustrated in FIG. 9. In this embodiment, the proximal end 52 of the tubular member 50 is preformed to cooperate with the ridge 28 and groove 29 of the shoulder area 27 and the distal end 43 of the retainer 40. It will be appreciated that the ridge 28 and the groove 29 of the shoulder area 27 of the hub 20, the distal end 43 of the retainer 40, and the flared portion 53 of the distal end 52 of the tubular member 50 are another possible embodiment of a means for retaining tubular member 50 in the hub 20 in sealing engagement. It will be appreciated by one skilled in the art that the retaining means may have various other configurations and perform the function thereof.

It will be appreciated that, although it is not illustrated, the distal end 57 of the tubular member 50 can include a tapered portion depicted in FIG. 6 in which the diameter of the tubular member 50 is gradually reduced. Such a tapered portion may be produced through known manufacturing methods such as drawings, sanding, grinding, heat forming or other similar processes.

FIGS. 4 and 6 are partially exploded cross-sectional views of the introducer sheath 10 in accordance with the present invention during different phases of the assembly process. To assemble the individual components described above into a completed introducer sheath 10, the distal end (not shown) of the tubular member 50 is passed through the central lumen 24 of the hub 20 as depicted in FIG. 4. The flared portion 53 of the proximal end 52 of the tubular member 50 is received proximate to the shoulder area 27 of the main body 21 of the hub 20. More specifically, in one embodiment depicted in FIG. 4, the flared portion 53 of the proximal end 52 of the tubular member 50 cooperates with the ridge 28 of the shoulder area 27 in the hub 20.

Next, as previously mentioned and now illustrated in FIG. 6, the retainer 40 is disposed into the central lumen 24 of the main body 21 of the hub 20. As a result, the distal end 43 of the retainer 40 contacts the flared portion 53 of the proximal end 52 of the tubular member 50. In one embodiment of the present invention, the optional angular teeth-like features formed in the interior surface of distal end 43 of retainer 40 contact and resiliently engage the flared portion 53 of the proximal end 52 of the tubular member 50. As illustrated in FIG. 6, the flared portion 53 of the tubular member 50 and the ridge 28 are configured to cooperate such that the tubular member 50 is retained in the distal end of the hub 20.

As the retainer 40 continues to be moved distally, the locking features 41 of the retainer 40 are received by corresponding locking features 26 formed within the second lumen portion 24b of central lumen 24 of the hub 20, thereby locking the retainer 40 and the tubular member 50 to the hub 20. As the distal end 43 of the retainer 40 moves toward the distal end 23 of the hub 30 until the locking features 41 and 26 engage, the flared portion 53 of tubular member 50 flexibly moves around the ridge 28 of the shoulder area 27 formed in the interior body 21 of the hub 20. When the locking features 41 and 26 engage, the distal end 43 of the retainer 40 has moved the flared portion 53 of the proximal end 52 around the ridge 28 and into the groove 29 such that both the distal end 43 of the retainer 40 and the proximal end 52 of the tubular member 50 are disposed in the groove 29 as illustrated in FIG. 6.

The flexible membrane 60 is now inserted into the proximal end 22 of the main body 21 of the hub 20. In particular, the distal end 62 of the flexible membrane 60 is disposed in the recess 45 formed in the proximal end 42 of the retainer 40. Next, the cap 30 is likewise inserted into the proximal end 22 of the main body 21 of the hub 20. The proximal end 63 of the flexible member 60 is disposed into the recess 31 formed in the outer surface 32 of the cap 30. As illustrated in FIG. 2, the retainer 40, the cap 30, and the main body 21 of the hub 20 cooperate to hold the flexible member 60 in place.

In one embodiment, the flared portion 53 of the tubular member 50 can be utilized to align the lumen of the tubular member 50 with central lumen 24 of the main body 21 of hub 20 such that a single axis bisects the flexible membrane 60, the hub 20, the retainer 40, the cap 30, and the tubular member 50.

As shown in FIGS. 2, 4 and 6, the main body 21 of the hub 20 can also include an aperture 25, wherein the aperture 25 is configured to be in fluid communication with the lumen 44 of the retainer 40 and the lumen 59 of the elongated tubular member 50. Although not shown, a flexible piece of tubing with a luer fitting or a valve assembly can be attached to the aperture 25 so that fluid can pass through the valve/luer and flexible tubing into the lumen 44 of the retainer 40 and the lumen 59 of the tubular member 50.

Alternatively, a finger grip (not shown) may be substituted in place of the valve/luer fitting and tubing in the event that the introducer is to be utilized with a vessel closure system such as that shown in U.S. patent application Ser. No. 10/356,214 filed Aug. 5, 2004 entitled "Clip Applier and Methods of Use" the entirety of which is hereby incorporated by reference.

Introducer sheath 10 also includes optional strain relief member 80 illustrated in FIGS. 1 and 2. In one embodiment strain relief member 80 is generally cup shaped and configured to cooperate with distal end 23 of hub 20. Strain relief member 80 has a central opening formed therein which is configured to receive elongated tubular member 50 therein. It will be appreciated that the strain relief member 80 may have various other configurations and perform the function thereof as long as is cooperates with distal end 23 of hub 20. In an alternate embodiment, strain relief member 80 and hub 20 are a unitary piece. It will be appreciated that strain relief member 80 and hub 20 may be made from differing materials.

Figure 7:
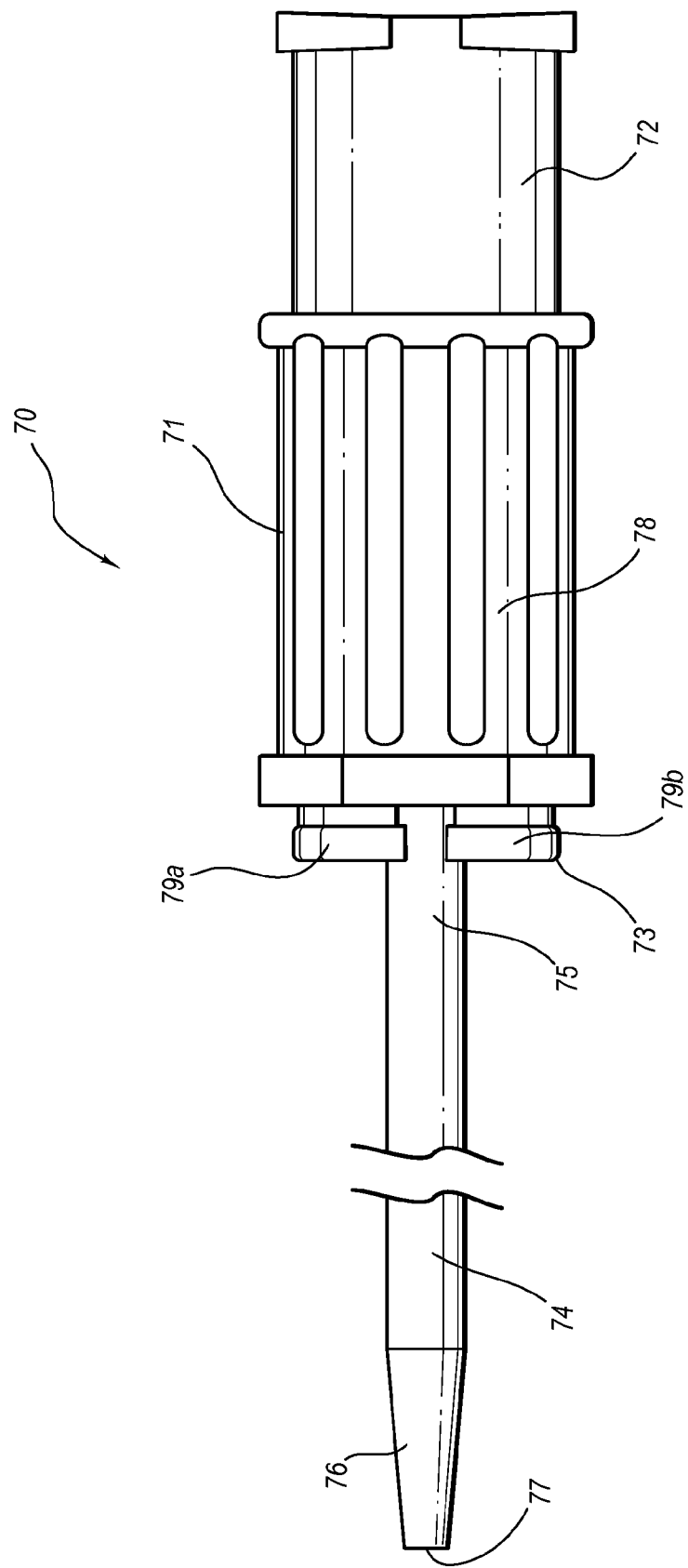
FIG. 7 is a partial elevation view of one exemplary embodiment of a dilator used with the introducer sheath of FIG. 2 in accordance with the present invention.
Figure 8:
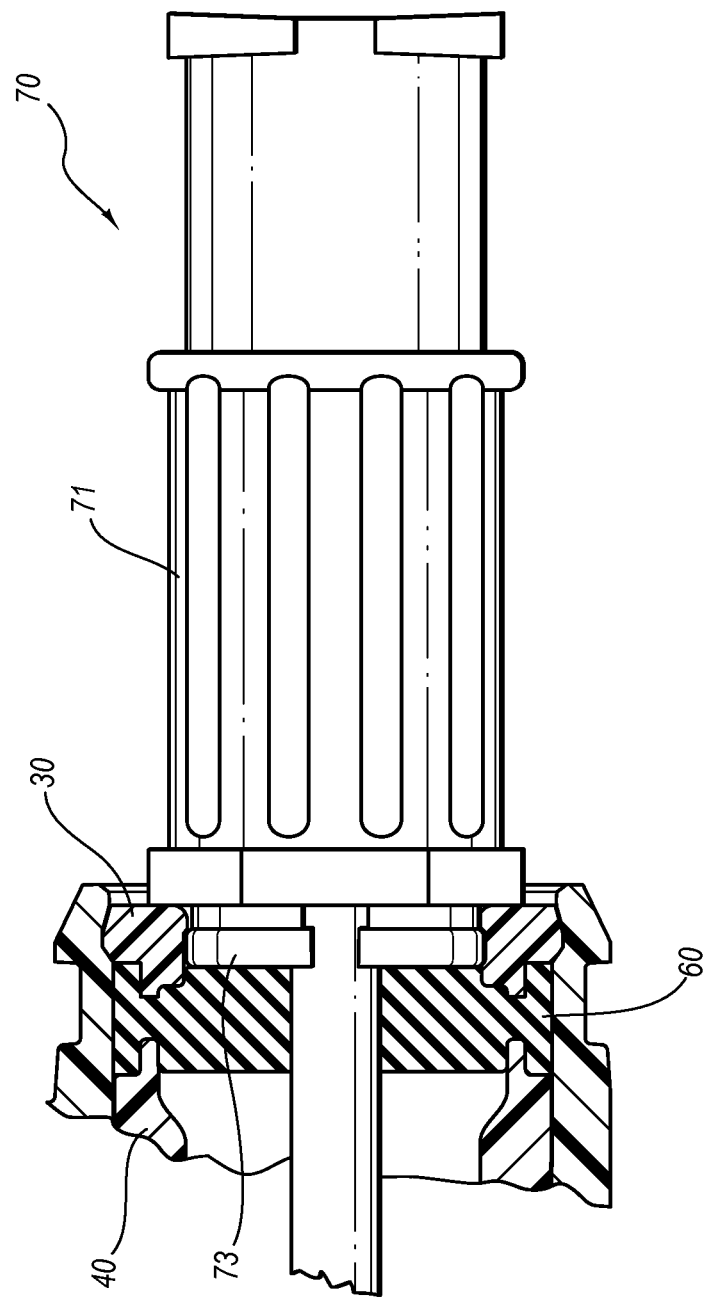
FIG. 8 is a partial cross-sectional, elevation view of the dilator of FIG. 7 attached to the introducer sheath of FIG. 2 in accordance with the present invention.

Referring now to FIG. 7, there is shown an exemplary embodiment of a dilator 70 that can be utilized in conjunction with the introducer sheath 10 of the present invention. The dilator 70 includes an elongated shaft member 74 having a proximal end 75 and a distal end 76. In one embodiment depicted in FIG. 7, the distal end 76 includes a tapered portion 77 configured for entering and expanding an opening in a vessel.

The dilator 70 also includes a handle 71 which has a proximal end 72 and a distal end 78. Distal end 78 of handle 71 is coupled to the proximal end 75 of the elongated shaft member 74. A resilient locking feature 73 is formed at the distal end 78 of the handle 71. As shown in FIG. 7, the locking feature 73 includes a first deflectable member 79a and a second deflectable member 79b which are configured to be received within the aperture 33 of the cap 30.

As illustrated in FIGS. 4 and 6, in one embodiment the aperture 33 of the cap 30 includes a ridge 34. When the resilient locking feature 73 of the handle 71 is disposed into the aperture 33, the first deflectable member 79a and the second deflectable member 79b resiliently deflect to pass over the ridge 34 until the first and second deflectable members 79a and 79b move back into position, thereby removably locking the handle 71 into place as illustrated in FIG. 9. The locking feature 73 of the dilator 70 is advantageous over conventional designs in that the first and second deflectable members allow for more consistent locking and release forces. In addition, the present invention increases the strength of the attachment between the cap 30 and the dilator 70. It will be appreciated that various other conventional methods for removably attaching the dilator 70 to cap 30 may be utilized. One skilled in the art would appreciate that this could include threaded engagements, and other types of mechanical attachments.

Figure 10:
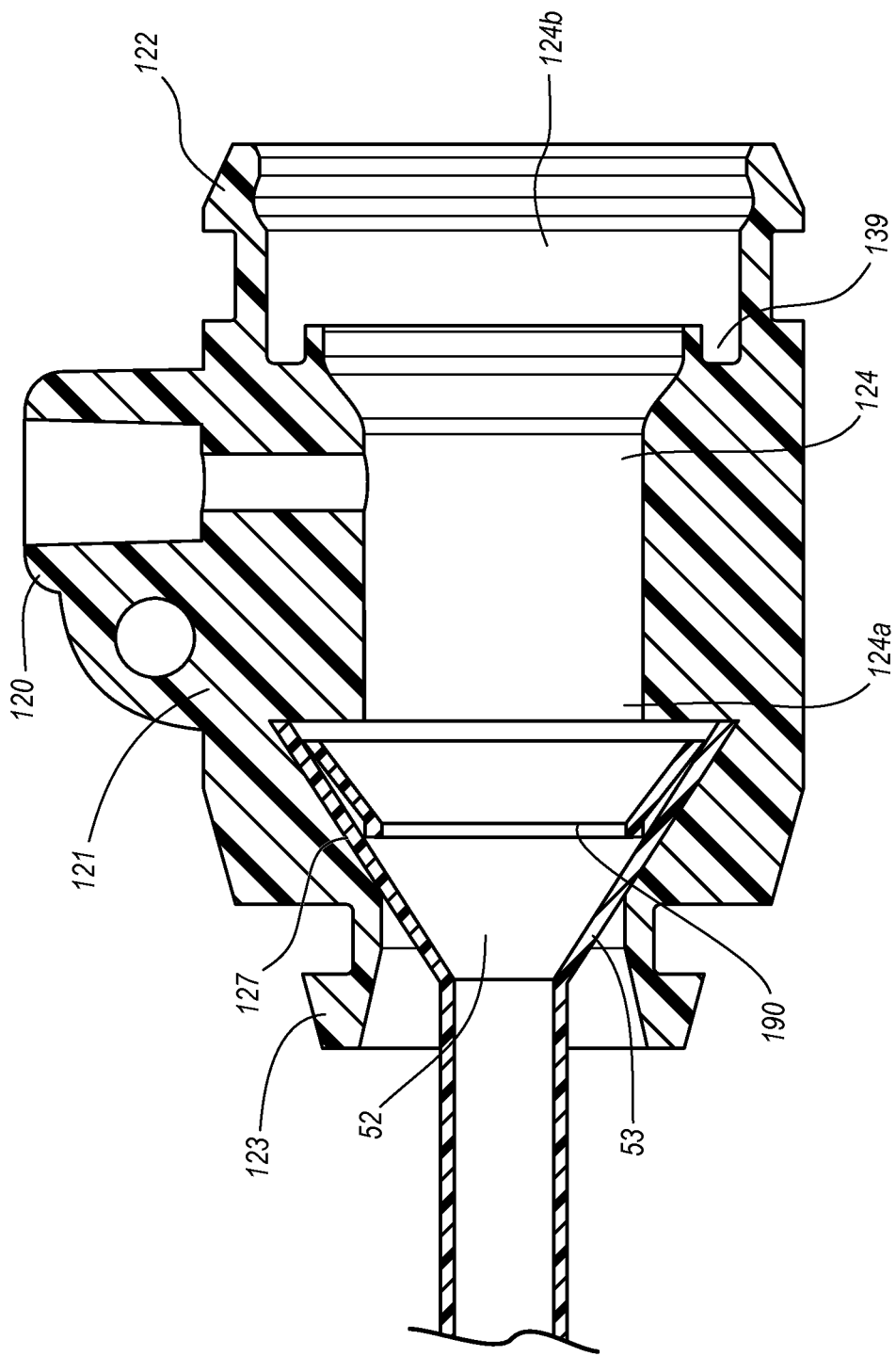
FIG. 10 is a partial cross-sectional view of an alternate embodiment of a portion of an overmolded introducer sheath in accordance with the present invention illustrating an overmolded hub, proximal end of the tubular member and a locking ring.

FIG. 10 depicts another embodiment of hub 120 in a different embodiment of an introducer sheath of the present invention. In this embodiment, the majority of the components of the introducer sheath 110 that were previously discussed are also compatible with the hub 120. Only the differences will be discussed in detail. The hub 120 includes a main body 121 having a proximal end 122 and a distal end 123 and a central lumen 124 extending therebetween. In this embodiment of the hub 120 depicted in FIG. 10, the central lumen 124 of the hub 120 comprises a first lumen portion 124a and a second lumen portion 124b. The first lumen portion 124a and the second lumen portion 124b have a common central axis. The first lumen portion 124a is proximate to the distal end 123 of the hub 120 while the second lumen portion 124b is proximate to the proximal end 122 of the hub 120. The second lumen portion 124b is sized and configured to receive the flexible membrane 60 and the cap 30 therein. This exemplary embodiment of the hub 120 has eliminated the need for a retainer such as retainer 40 illustrated in FIG. 4. In one embodiment, the first lumen portion 124a and the second lumen portion 124a are of differing size.

In the embodiment of the hub 120 depicted in FIG. 10, in this embodiment the introducer sheath includes a lock ring 190. FIG. 11a depicts one exemplary embodiment of a lock ring 190. Lock ring 190 has a distal portion 192 and a proximal portion 194. In one embodiment of the lock ring 190 illustrated, the distal portion 192 has a rounded outer peripheral shape. It will be appreciated that the distal portion 192 could have various other shapes as long as it is shaped and configured to cooperate with first lumen portion 124a. By way of example and not limitation, the shape of distal portion 192 of lock ring 190 could be oval, elliptical or various combinations thereof. The distal portion 194 of the lock ring 190 is configured to cooperate with flared portion 53 of proximal end 52 of tubular member 50. In an exemplary embodiment, the proximal portion 194 of lock ring 190 is flared as illustrated.

In the exemplary embodiment, of the lock ring 190 illustrated in FIG. 11a, the lock ring 190 includes posts 196 which are formed on the exterior surface of the lock ring 190. In one embodiment, posts 196 extend along the outer surface of the lock ring 190 and in this embodiment are substantially parallel to the central axis of the introducer sheath. In the exemplary embodiment depicted in FIG. 11a, the posts 196 extend on the outer surface of the distal portion 192 of lock ring 190 and along the proximal portion 194 until the angle of the flare intersects them. It will be appreciated that the posts 196 could have differing sizes and lengths. In exemplary embodiment illustrated in FIG. 11a, the lock ring 190 has four posts 196 which are equally spaced along the exterior surface of the lock ring. It will be appreciate that differing numbers of posts 196 as well as different spacing of the posts 196 could be utilized.

FIG. 11b illustrates another embodiment of a lock ring 290 for use in an introducer sheath of the present invention. In this embodiment, lock ring 290 has a distal portion 192 and a flared proximal portion 194 but does not include the posts 196.

With the embodiment of introducer sheath which uses a lock ring and eliminates the need for a retainer, the hub 120 is formed using a conventional overmolded platform in which the flared portion 53 of proximal end 52 of tubular member 50 and lock ring 190 are positioned and hub 120 is molded around them. In one embodiment, the angle of the flare of the flared portion 53 is about 30 to about 35 degrees from the central axis. It will be appreciate that various other angles of the flare for flared portion 53 can be used as long as flared portion 53 is configured to cooperate with lock ring 190 and shoulder area 127. Once molded, the lock ring 190, the flared portion 53 of proximal end 52 of tubular member 50, and hub 120 form a fluid tight seal.

In the embodiment illustrated in FIG. 10, the distal end 57 of the tubular member 50 extends outwardly from hub 120. The flared portion 53 of the proximal end 52 of the tubular member 50 is proximate to the shoulder area 127 of the main body 21 of the hub 120. In an exemplary embodiment of the present invention, the beginning of flared portion 53 is located generally proximate to the distal end 123 of the hub 120. It will be appreciate that various lengths of flared portion 53 and locations of the beginning of flared portion 53 can be utilized and still perform the function thereof.

The distal portion 192 of the lock ring 190 cooperates with the flared portion 53 of proximal end 52 of tubular member 50. In this embodiment, the proximal end 122 of the hub 120 is configured to cooperate with the distal end 62 of flexible membrane 60. In this exemplary embodiment of the hub 120, the second lumen portion 124b is configured to receive flexible membrane 60 therein. As illustrated in FIG. 10, the hub 120 has a channel 139 formed therein which is configured to receive the distal end 60 of flexible membrane 60 therein. The remainder of the assembly of the introducer sheath is consistent with that previously discussed.

In accordance with the present invention, an introducer sheath or components thereof can be formed using one or more materials. Typically, the materials used in forming the introducer sheath are medical grade synthetic materials or plastics. Exemplary materials may include, but are not limited to, flexible PVC, polyurethane, silicone, liner low-density polyethylene ("LLDPE"), polyethylene, high density polyethylene, ("DUPE"), polyethylene-lined ethylvinyl acetate ("PE-EVA"), polypropylene, latex, thermoplastic rubber, polytetrafluoroethylene (PTFE), expandable polytetrafluoroethylene (ePTFE), fluoroethylene-propylene (FEP), perfluoroalkoxy (PFA), ethylene-tetrafluoroethylene-copolymer (ETFE), ethylene-chlorotrifluoroethylene (ECTFE), polychloro-trifluoroethylene (PCTFE), polyimide (PI), polyetherimide (PEI), polyetherketone (PEEK), polyamide-imide (PAI), other fluoropolymers, and the like.

Exemplary materials used in the introducer sheath or the components of the sheath can also include elastomers or thermoplastic elastomers. Examples of elastomers include, but are not limited to, natural rubber, silicone rubber, polyurethane rubber, polybutadiene, polyisoprene, chlorosulfonated polyethylene, polysulfide rubber, epichlorohydrin rubber, ethylene propylene rubber, and the like or any combination thereof. These materials provide the elasticity that enable the sheath to expand and/or contract to accommodate the removal/insertion of a medical device as required. Other materials that can be used can include, but are not limited to, dip coated type silicones.

In other embodiments, the materials suitable for use in an introducer sheath and the components thereof are configured to have chemical resistance, crack resistance, no toxicity, Food and Drug Administration ("FDA") compliance, non-electrically conductive, dimensional stability, and/or be sterilized by ethylene oxide, gamma radiation, autoclave, UV light, ozone, and the like.

In addition, the selection of materials for a particular introducer sheath or its components can depend on a variety of factors that include, but are not limited to, a particular stiffness and/or flexibility of the sheath or any portion of the sheath, including the desired column stiffness and strength to enable insertion of the sheath, a particular shear or split strength for the sheath or any portion of the sheath, the ability to resist kinking, and the like. For example, the material used for the tubular portion of the introducer sheath may be selected based on shear strength or how easily it can be split. Further, certain features of the sheath may be formed to enhance certain characteristics. For example, a strain relief portion may be formed so as to resist kinking while the elongated tubular portion may be formed to facilitate splitting.

When more than one material is used to form the sheath or to form specific portions of the introducer sheath, the materials may be selected, in addition to the factors identified herein, on a bond strength between the materials or on the elasticity of a particular material. The bond strength, for example, may have an impact on the splitability of the sheath or of a portion of the sheath. The bond strength may also affect the ability of the sheath to expand without splitting.

When an elastomer is used in the sheath or a component of the sheath, the elasticity of the elastomer enables the sheath or a portion of the sheath to at least partially deform, resiliently deform, or elastically expand as needed to accommodate a medical device and then return or substantially return to its configuration prior to deforming or expanding. Advantageously, the ability to deform and/or expand permits a device, such as an expanded or expandable balloon, to be withdrawn through the sheath without removing the sheath, for example from a patient's vasculature. This maintains access to the patient's vasculature without the difficulty of inserting another sheath or medical device through the puncture site. Further, maintaining the introducer sheath in place allows a physician or technician to insert one or more additional medical devices, such as a vessel closure device, using the introducer sheath. It will be appreciated that the introducer sheath will be used in a variety of medical procedures.

For example, the introducer sheaths disclosed herein are intended to be utilized in combination with a vessel closure device such as those shown in U.S. Pat. No. 6,197,042 and pending U.S. patent application Ser. No. 10/356,214, filed Aug. 8, 2004 entitled "Clip Applier and Methods of Use", which are both assigned to a common owner and are hereby incorporated by reference herein in their entireties.

In one embodiment, the hub 20, the retainer, and the cap, may be constructed of materials such as acrylonitrile butadiene styrene (ABS), polyvinylchloride (PVC), polycarbonate. In one embodiment, the hub 20 is formed through injection molding. Any of the materials may further include glass reinforcement particles mixed therewith.

In an exemplary embodiment, the elongated tubular member 50 is constructed of polytetrafluoroethylene, Teflon, and similar materials. In one embodiment the tubular member 50 is generally fabricated through extrusion. The tubular member 50 as described herein may be constructed of a single material or may be constructed of more than one material. For example, the tubular member 50 may be constructed of two or more materials by utilizing a co-extrusion process.

It will be appreciated by one skilled in the art, that various other materials can be used for these individual components. For example, any of the above identified materials may further include glass reinforcement particles mixed therewith. Further, various other methods of manufacture could be utilized.

Further still, it is contemplated that a geometric feature may be formed within the wall of the tubular member 50. An example of such feature is a sinusoidal pattern formed within the wall of the tubular member 50. The sinusoidal pattern may be beneficial in that it may promote easier splitting of the sheath if desired. Additionally, an introducer sheath having this type of pattern may also reduce friction between the sheath and medical devices disposed through the sheath as the medical device will only contact the sheath at various points along the length of the sheath versus contacting the wall of the sheath along the entire length of the sheath.

Although the present invention has been described with regard to specific designs and materials, it shall not be considered limiting in any manner. For example, materials not described herein may be utilized as well as methods and processes.

Although the present invention has been described with regard to specific designs and materials, it shall not be considered limiting in any manner. For example, materials not described herein may be utilized as well as methods and processes.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An introducer sheath, comprising:
a hub having a proximal end and a distal end and a lumen extending therebetween, the hub having a cutout in the proximal end thereof;
an elongated tubular member having a proximal end and a distal end, the elongated tubular member being an outermost surface of the introducer sheath;
a retaining member having an outer surface parallel to an inner surface defining a lumen, the retaining member sized to be received within the lumen of the hub and being further configured to retain the proximal end of the tubular member within the lumen of the hub and receive a portion of the proximal end of the elongated tubular member about the outer surface and within the lumen of the retaining member, the retaining member being configured to be frictionally restrained within the lumen of the hub;
a flexible membrane having an opening and a locating channel, the flexible membrane being secured within the hub; and
a cap having a protrusion configured to fit within the cutout of the hub in a manner that secures the cap to the hub, a portion of the cap being configured to fit into the locating channel in the flexible membrane in a manner that locates the cap relative to the flexible membrane, and the flexible membrane and the cap cooperating to further secure the retaining member in the hub.

2. The introducer sheath of claim 1, further including a strain relief portion adjacent the distal end of the hub and adjacent the proximal end of the tubular member, the tubular member being substantially straight from the distal end to the strain relief portion.

3. The introducer sheath of claim 1, wherein the flexible membrane is a flexible valve member.

4. The introducer sheath of claim 3, wherein the valve member is additionally in fluid communication with the retaining member.

5. The introducer sheath of claim 4, wherein the valve member has an opening formed therein; and
the cap is configured such that upon being disposed over the valve member, the cap provides a compressive force to the valve member which causes the opening in the valve member to be squeezed, thereby increasing the strength of the seal without reducing access to the lumen of the hub.

6. The introducer sheath of claim 1, further comprising an aperture extending through a wall of the hub.

7. The introducer sheath of claim 1, wherein the elongate tubular member includes an outer wall and an inner wall thereby defining a thickness, and a pattern fanned within the inner wall.

8. An introducer sheath, comprising:
a hub having a proximal end and a distal end and a lumen extending therebetween, the hub having a cutout in the proximal end thereof;
a flexible valve member disposed in the distal end of the hub, the flexible valve member having an opening and a locating channel, the flexible valve member being secured within the hub;
an elongated tubular member having a proximal end and a distal end, the elongated tubular member being an outermost surface of the introducer sheath;
a retaining member having a proximal end and a distal end and being configured to be received within the lumen of the hub, the proximal end of the retaining member being configured to receive a portion of the flexible valve member and an inner surface of the distal end of the retaining member being configured to contact the flared portion of the tubular member such that the proximal end of the tubular member is retained within the lumen of the hub upon the retaining member being received in the hub, the retaining member being configured to be frictionally restrained within the lumen of the hub, the elongated tubular member abutting a proximally facing surface of the distal end of the hub and the distal end of the retaining member; and
a cap having a protrusion configured to fit within the cutout of the hub in a manner that secures the cap to the hub, a portion of the cap being configured to fit into the locating channel in the flexible valve member in a manner that locates the cap relative to the flexible valve member, and the flexible valve member and the cap cooperating to further secure the retaining member in the hub.

9. The introducer sheath of claim 8, wherein the distal end of the retaining member, the hub, and the proximal end of the tubular member form a fluid seal.

10. The introducer sheath of claim 8, wherein:
the hub further comprises a first locking feature formed in the lumen thereof;
the retaining member further comprises a second locking feature formed in the outside surface thereof, the second locking feature of the retaining member resiliently engages the first locking feature upon the retaining member being disposed in the lumen of the hub.

11. The introducer sheath of claim 8, further comprising a dilator configured to removably cooperate with the cap.

12. The introducer sheath of claim 11, wherein the dilator comprises a handle having a resilient locking feature configured to be removably disposed in the cap.

13. The introducer sheath of claim 12, wherein the locking feature of the handle comprises at least one resilient member configured to be removably disposed in the cap.

14. The introducer sheath of claim 13, wherein:
the cap has an aperture formed therein; and
the at least one resilient member is configured to be resiliently disposed in the aperture of the cap.

15. The introducer sheath of claim 8, further comprising a strain relief portion adjacent the distal end of the hub.

16. An introducer sheath, comprising:
a hub having a proximal end and a distal end with a lumen extending therebetween, the lumen of the hub having a groove with a proximally oriented opening formed therein, the hub having a cutout in the proximal end thereof;
an elongated tubular member having a proximal end and a distal end, the proximal end of the tubular portion having flared portion, a distal portion extending from the distal end toward the proximal end and including a midpoint of the elongated tubular member, the elongated tubular member being an outermost surface of the introducer sheath: and
a retaining member having a proximal end, a distal end, an outer surface extending from the proximal end toward the distal end and being parallel to an inner surface defining a lumen extending from the proximal end toward the distal end, the distal end of the retaining member being configured to be received in the groove formed in the lumen of the hub, the distal end of the retaining member being configured to contact the flared portion of the tubular member when the distal end of the retaining member is disposed in the groove and receiving a portion of the flared portion about the outer surface and within the lumen of the retaining member in a sealing engagement, the retaining member having a recessed portion proximal to the distal end thereof, the retaining member being configured to be frictionally restrained within the lumen of the hub;
a flexible membrane having an opening, a first locating channel and a second locating channel, the recessed portion of the retaining member being configured to enter the first locating channel and to locate the flexible membrane relative to the retaining member; and
a cap having a protrusion configured to fit within the cutout of the hub in a manner that secures the cap to the hub, a portion of the cap being configured to fit into the second locating channel in the flexible membrane in a manner that locates the cap relative to the flexible membrane, and the flexible membrane and the cap cooperating to further secure the retaining member in the hub.

17. The introducer sheath of claim 16, wherein the distal end of the retaining member, the flared portion of the tubular member and the hub form a seal.

18. The introducer sheath of claim 16, further comprising a dilator configured to removably cooperate with the cap, the dilator having a resilient locking feature configured to be removably disposed in the aperture in the cap.

19. An introducer sheath, comprising:
a hub having a proximal end and a distal end and a lumen extending therebetween, the hub having a cutout in the proximal end thereof, the hub having a locking feature located in the lumen thereof;
an elongated tubular member having a proximal end and a distal end, the elongated tubular member being an outermost surface of the introducer sheath;
a retaining member having an outer surface parallel to an inner surface defining a lumen, the retaining member configured to be received within the lumen of the hub, the retaining member being configured to secure the elongated tubular member to the hub, the retaining member having one or more locking features configured to engage the locking feature of the hub, thereby securing the retaining member within the lumen of the hub, the elongated tubular member abutting a proximally facing surface of the distal end of the hub and the distal end of the retaining member; and a flexible membrane having an opening and a locating channel, the flexible membrane being secured within the hub; and a cap having a protrusion configured to fit within the cutout of the hub in a manner that secures the cap to the hub, a portion of the cap being configured to fit into the locating channel in the flexible membrane in a manner that locates the cap relative to the flexible membrane, and the flexible membrane and the cap cooperating to further secure the retaining member in the hub.

20. The introducer sheath of claim 19, wherein said retaining means further comprises:

a shoulder portion formed in the hub; and the distal end of the retaining member configured cooperate with the shoulder portion formed in said hub.

21. The introducer sheath of claim 20, wherein the shoulder portion in the hub has a groove formed therein configured to cooperate with the distal end of the retaining member.

22. The introducer sheath of claim 21, wherein the distal end of the retaining member is configured to be received in the groove formed in the shoulder portion of the hub.

23. The introducer sheath of claim 19, wherein upon the retaining member being received in the lumen of the hub, the distal end of the retaining member engages a flared portion of the proximal end of the tubular member such that the tubular member is retained within the lumen of the hub in a sealing engagement with the hub and the retaining member.

24. The introducer sheath of claim 19, further comprising:

a first locking feature formed in the lumen of the hub;

a second locking feature formed in the outside surface of the retaining member configured to cooperate with the first locking feature formed in the lumen of the hub.

25. An introducer sheath comprising individual components that are configured so as to be assembled using only resilient connections, the introducer sheath comprises:

a hub having a proximal end and a distal end and a lumen extending therebetween;

an elongated tubular member having a proximal end and a distal end, the proximal end of the tubular member having a flared portion, the tubular member being substantially straight from the distal end toward the proximal end and including a midpoint of the elongated tubular member, the elongated tubular member being an outermost surface of the introducer sheath;

a retaining member having an outer surface parallel to an inner surface defining a lumen, the retaining member being configured to be received within the lumen of the hub and to retain the proximal end of the tubular member within the lumen of the hub and being configured to receive a portion of the proximal end of the elongated tubular member about the outer surface of the retaining member and within the lumen of the retaining member such that the proximal end of the tubular member is retained within the lumen of the hub upon the retaining member being received in the hub, the retaining member having a recessed portion proximal to the distal end thereof, the retaining member being configured to be frictionally restrained within the lumen of the hub, the elongated tubular member abutting a proximally facing surface of the distal end of the hub and the distal end of the retaining member;

a flexible valve disposed in the lumen of the hub at the proximal end of the hub the flexible valve having a locating channel configured to accept the recessed portion of the retaining member; and a cap removably secured to the hub at the proximal end of the hub, a portion of the cap being configured to fit into the locating channel in the flexible valve member in a manner that locates the cap relative to the flexible valve membrane, and the flexible valve member and the cap cooperating to further secure the retaining member in the hub.

\* \* \* \* \*